United States Patent [19]

Bigham

[11] 4,364,376
[45] Dec. 21, 1982

[54] METHOD AND DEVICE FOR INJECTING A BOLUS OF MATERIAL INTO A BODY

[76] Inventor: Keith E. Bigham, 178 Triangle St., Danbury, Conn. 06810

[21] Appl. No.: 94,355

[22] Filed: Dec. 26, 1979

[51] Int. Cl.³ .............................................. A61N 5/12
[52] U.S. Cl. ...................................... 128/1.1; 128/215
[58] Field of Search ................ 128/1.1, 213, 215, 216, 128/218 R, 218 D, 218 DA, 218 G, 220, 234, 260–265, 273.3, 278, 760–766

[56] References Cited

U.S. PATENT DOCUMENTS

| | | | |
|---|---|---|---|
| 1,830,453 | 11/1931 | Wassmer | 128/1.1 X |
| 1,930,929 | 10/1933 | Eisenberg | 128/218 G |
| 2,390,246 | 12/1945 | Folkman | 128/218 D |
| 3,957,033 | 5/1976 | Winchell et al. | 128/1.1 |
| 4,073,288 | 2/1978 | Chapman | 128/766 |
| 4,241,728 | 12/1980 | Mirell | 128/1.1 |

Primary Examiner—John D. Yasko

Attorney, Agent, or Firm—St. Onge, Steward, Johnston & Reens

[57] ABSTRACT

A radiation protective device for use in the injection of a bolus of radioactive material into a blood vessel is described. A bolus retainer is used having a bolus chamber sized to retain a desired bolus size. The chamber extends between front and rear ends of the bolus retainer which fits within a radiation shield. The front end is adapted to be connected to a hypodermic needle. The rear end is adapted for connection to a first syringe sized to precisely draw in the desired bolus size and a flushing syringe to advance the bolus into a blood vessel through the hypodermic needle. The bolus retainer has a valve located near its rear end to retain the bolus in the chamber when the flushing syringe is inserted to replace the first syringe. An improved technique for administering a radioactive bolus is described with substantially less radiation exposure and improved control and speed over the bolus injection.

3 Claims, 8 Drawing Figures

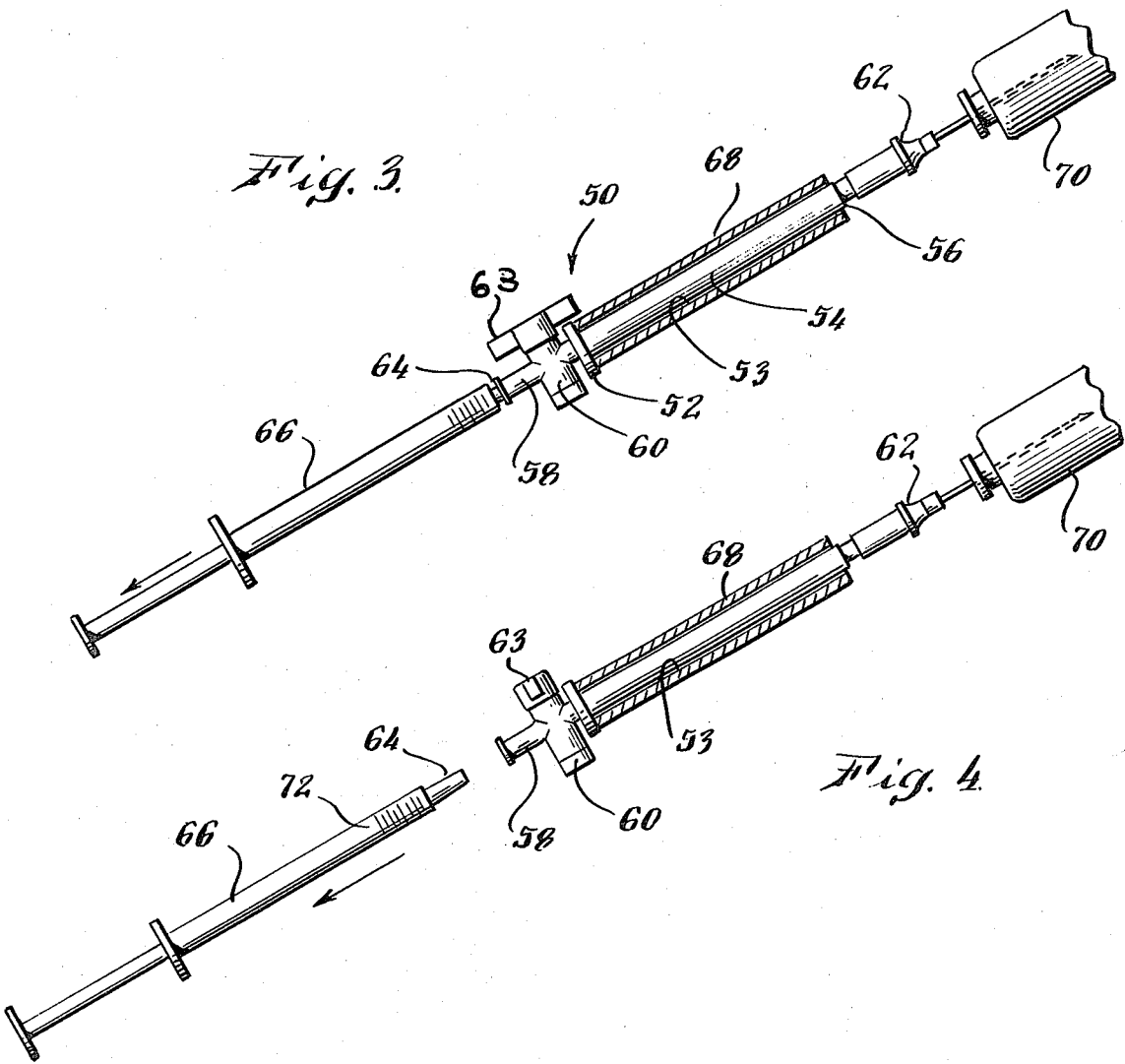
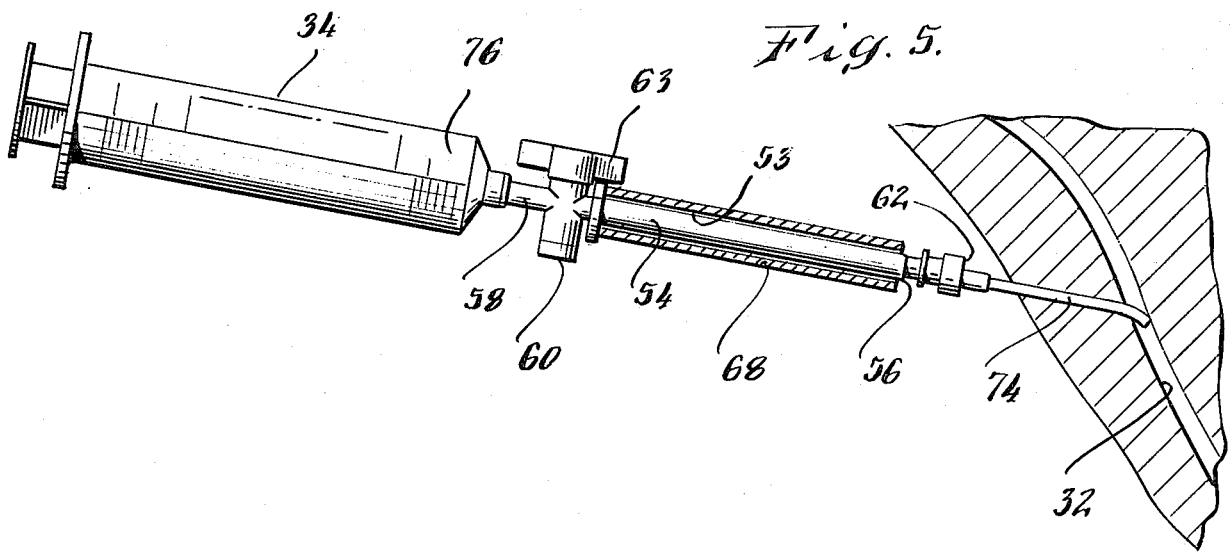

METHOD AND DEVICE FOR INJECTING A BOLUS OF MATERIAL INTO A BODY

FIELD OF THE INVENTION

This invention relates to a device and method for injecting a bolus of a material into a body. More specifically, this invention relates to a device and method for injecting a bolus of radioactive material in a nuclear medical procedure.

BACKGROUND OF THE INVENTION

In nuclear medicine procedures, a bolus of radioactive liquid is injected into a blood vessel. The progress or dispersal of the bolus is monitored by a radioactive sensing system with which one may then obtain an indication of heart or other vascular diseases.

Prior art techniques in the injection of a radioactive bolus typically involve apparatus as depicted in FIGS. 1 and 2. Thus, a syringe 10 is inserted into a vial 12 containing a radioactive liquid 14.

The amount or size of the bolus taken in by syringe 10 would depend upon the radioactive dosage needed for the particular procedure, the person in whose blood system the bolus is to be injected and such other factors as are generally well understood in the nuclear medicine field.

The filled or partially filled syringe 10 is then placed on an input port 16 of a three-way conventional valve 18 controlled by a manual control cock 20 and having another input port 22. An output port 24 is connected to a long flexible tube 26 which, at one end 28, is connected to a hypodermic needle 30 placed in a catheter inserted in a blood vessel 32. A flushing syringe 34 containing a supply of sterile saline solution is applied to input port 22.

To avoid the insertion of a significant amount of harmful air into blood vessel 32, the flushing syringe 34 is first actuated to fill flexible tube 26 with saline solution while the needle 30 is out of vessel 32. Thereupon, the valve 20 is actuated so that the radioactive bolus 36 in syringe 10 can be moved into tube 26 such as at 38 by emptying the syringe 10.

The valve 20 is then changed so that saline solution from flushing syringe 34 can be inserted into tube 26 behind bolus 36 and thus advance the bolus 36 for injection into blood vessel 32.

Since the bolus 36 is a radioactive substance, it is normal practice to protect the technician, physician or nurse who is administering the bolus against radiation with a lead shield 40 in the form of a cylinder and sized to fit over syringe 10. The shield, although affective when installed, is not able to protect the user throughout the procedure. Thus, after initial take-up of the bolus 36 in syringe 10 when the bolus is transferred to the flexible tube 26 at 38 the person applying the procedure is exposed to radiation. Though the radiation level for any one bolus is low, the administering of many tests can result in the accumulation of a radiation dosage which is extremely hazardous over an extended time period.

SUMMARY OF THE INVENTION

With an apparatus and method in accordance with the invention, the radiation exposure to a person who administers a radioactive bolus can be effectively reduced. This is achieved by employing a bolus retainer which, at a front end, is adapted to be attached to a bolus intake and discharge nozzle such as a hypodermic needle and at a rear end to a syringe. A manual control valve is located near the rear end to open or close a bolus chamber which extends between the front and rear ends of the bolus retainer.

The initial take-up of a radioactive bolus is done by attaching an empty syringe to the rear end of the bolus retainer and a hypodermic needle to its front end. A bolus of suitable size is then drawn from a vial into the bolus retainer by actuating the syringe while a lead shield is employed around the bolus retainer. The amount of bolus drawn from the vial does not require visibility of the bolus retainer since the bolus taken in can be precisely determined from the graduations on the syringe.

Once a bolus is placed inside the bolus retainer, the first syringe is replaced with a flushing syringe containing a sterile supply of saline solution. The bolus can then be injected by actuating the flushing syringe to advance the saline solution through the bolus retainer and thus push the bolus out through the nozzle or hypodermic needle into a blood vessel while the lead shield remains in place.

Hence, with a bolus retainer in accordance with the invention, a lead shield can be employed throughout the entire procedure, thus minimizing radiation exposure hazards. Furthermore, a more precise control over the bolus injection procedure can be maintained since a flexible tube such as 26 is shown in FIG. 2 is not needed. The bolus injection system in accordance with the invention is able to provide improved bolus flow rate characteristics and also able to deliver a significantly greater percentage of the measured bolus to the patient.

It is, therefore, an object of the invention to provide a device and method for improving the injection of a bolus of a material into a blood vessel. It is a further object of the invention to provide an apparatus and method to reduce the radiation exposure hazard in the injection of a bolus of radioactive material in a nuclear medicine procedure.

These and other objects and advantages of the invention can be understood from the following detailed description of an embodiment as described in conjunction with the drawings.

BRIEF DESCRIPTION OF DRAWINGS

FIG. 3 is a side view in elevation and partial section of an apparatus in accordance with the invention and used in a procedure to inject a bolus in a blood vessel;

FIG. 4 is a similar side view of the apparatus as shown in FIG. 3 but for a subsequent step in the procedure for injecting a bolus;

FIG. 5 is a side view in elevation and partial section of the apparatus in accordance with the invention during its use in the injection of the bolus in a blood vessel;

DETAILED DESCRIPTION

Figure 1:
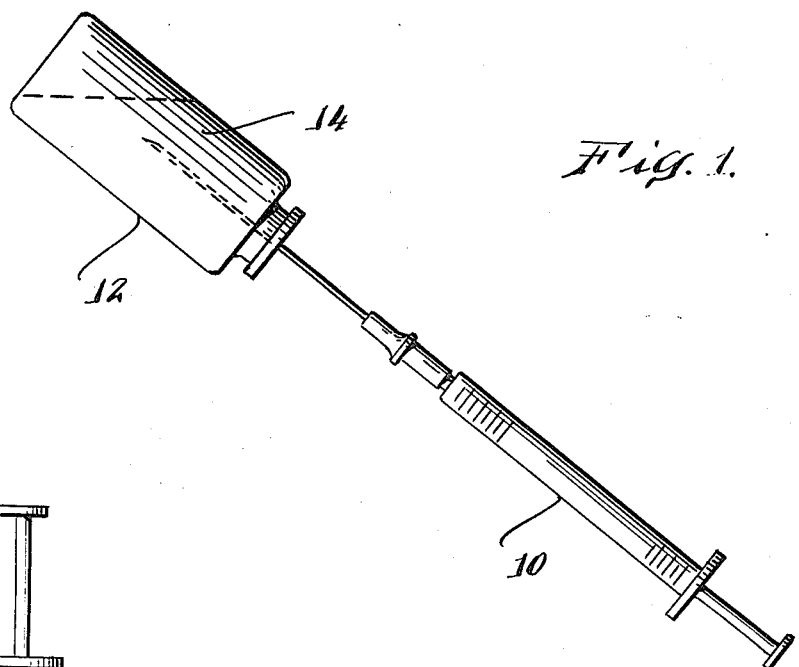
FIG. 1 is a side view in elevation of devices employed in the prior art technique of injecting a bolus of radioactive liquid in a blood vessel.
Figure 2:
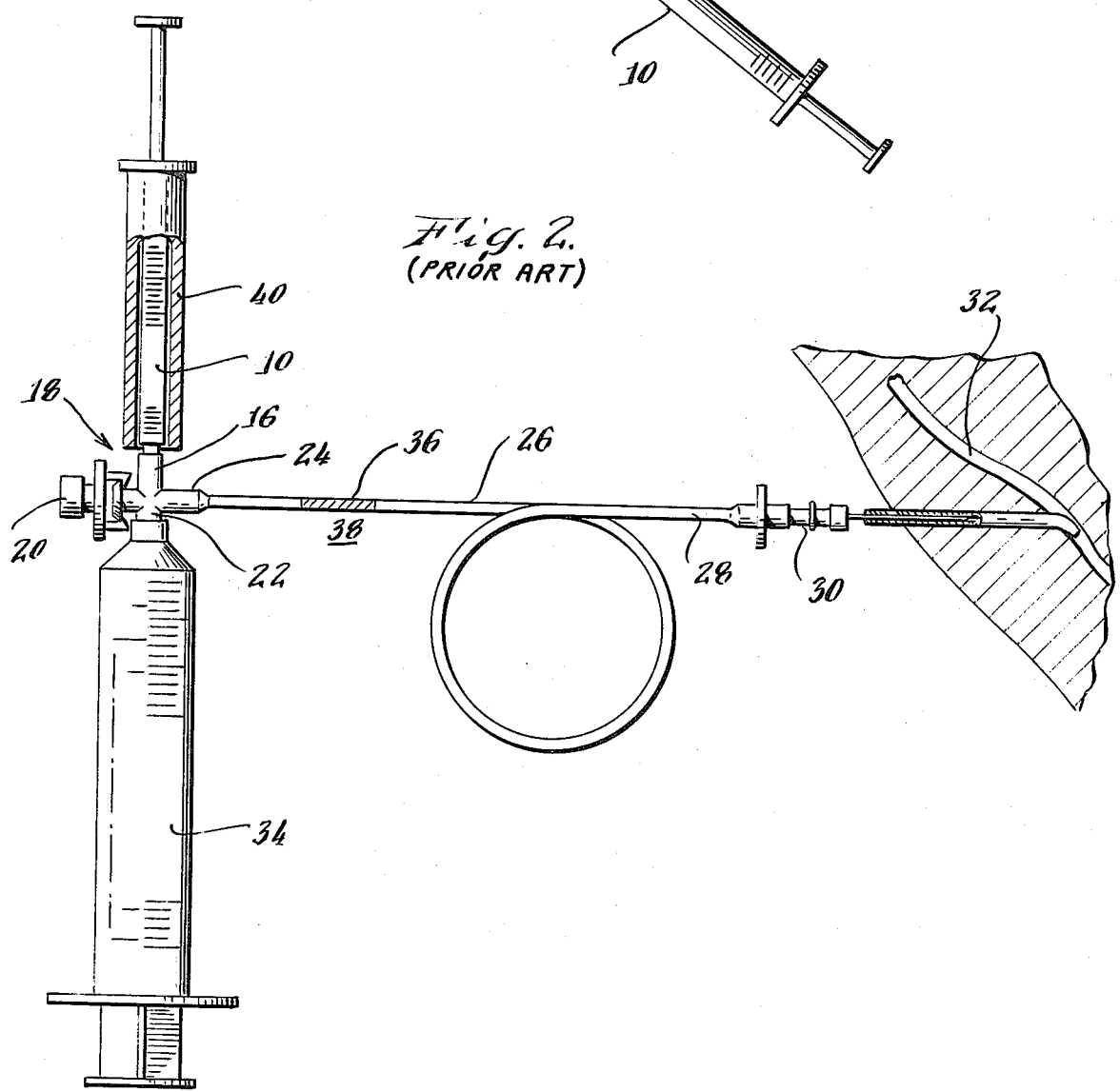
FIG. 2 is a side view in elevation and partial section of prior art devices employed in the injection of a bolus of radioactive material in a blood vessel.

With reference to FIGS. 3 through 5, a device 50 for injecting a bolus in accordance with the invention is shown. A bolus retainer 52 is provided in the form of a hollow cylindrical body 53 having a bolus chamber 54 in the form of a through bore extending between front end 56 and rear end 58. A manual control valve 60 is mounted near rear end 58 to open or close chamber 54 from rear end 58.

The front end of bolus retainer 52 is shaped and sized to sealingly engage a nozzle in the form of a hypodermic needle 62. The latter could be permanently attached to bolus retainer 52, but preferably is separately obtained as a conventional separate sterile needle. Attachment of front end 56 to hypodermic needle 62 involves a conventional simple push-on engagement as is well known in the art.

The valve 60 is an integral part of bolus retainer 52 and provides two positions, open as shown in FIG. 3 with the valve handle 63 in the indicated position, or closed as shown in FIG. 4. Valve 60 is a conventional plastic valve as is commonly available. The entire bolus retainer 52 is formed of a plastic material and is packaged in a sterile container (not shown).

The rear end 58 is adapted for releasable attachment to the working end 64 of a conventional syringe 66 which is attached to end 58 in a conventional push-on pull-off manner. The rear end 58 is shown in a straight alignment with the bolus chamber 54, though it should be understood that other alignments, such as at a right angle, could be employed.

The body 53 in which the bolus 36 is retained is shaped to be enclosed by a radioactive shield 68 in the form of a hollow lead cylinder. The shield 68 may be frictionally held to the outer surface of body 53 while the bolus injection device 50 is used from the time the bolus is initially drawn from a vial 70 as shown in FIG. 3.

The use of lead shield 68 hides the body 53 from view while a bolus is drawn from vial 70 by syringe 66. The graduations such as at 72 on syringe 66, however, enable a precise determination of the amount of radioactive liquid drawn from vial 70.

After a bolus of radioactive liquid has been drawn from vial 70, valve 60 is closed and syringe 66 disengaged as shown in FIG. 4. A different flushing syringe such as 34 is then attached to end 58 of bolus retainer 52. Syringe 34 as previously described contains a sterile saline solution to advance the bolus in retainer 52 into blood vessel 32 as shown in FIG. 5.

Figure 6:
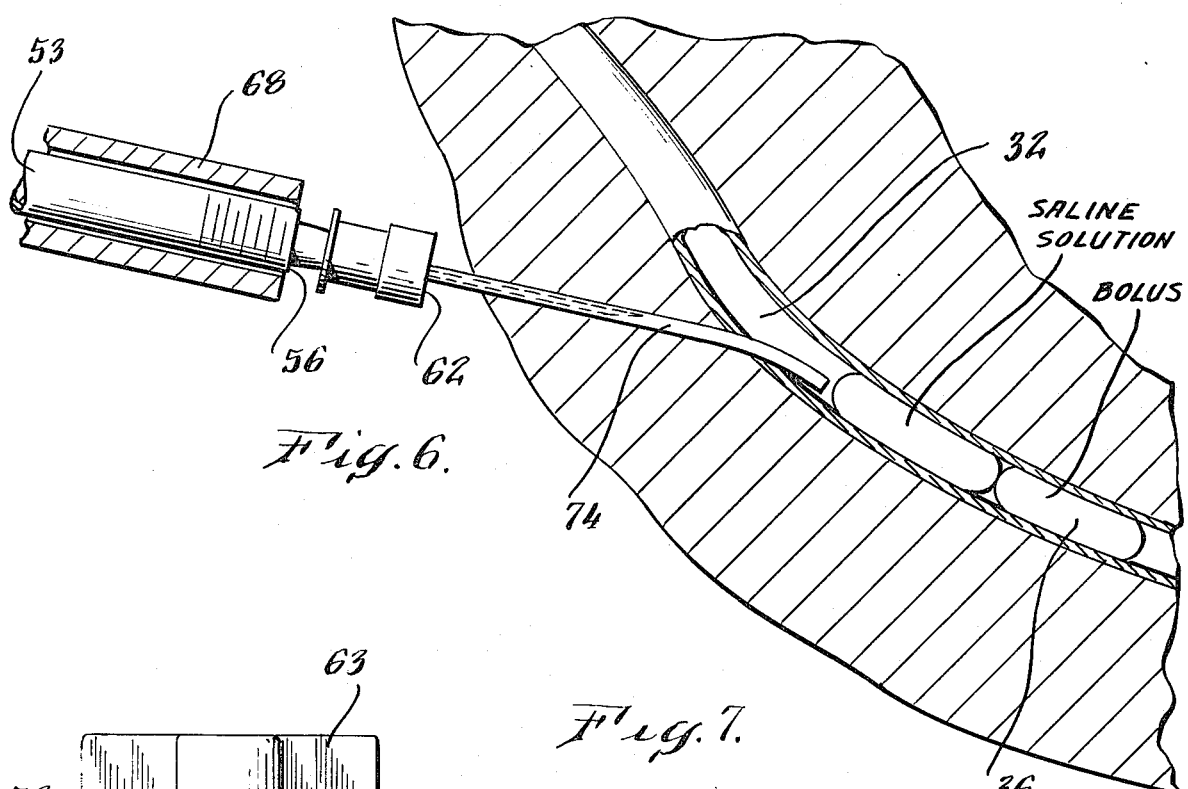
FIG. 6 is an enlarged partial sectional view of a portion of the view of FIG. 5.

The hypodermic needle 62 is placed in a cannula 74 previously inserted through an opening in the body to extend into blood vessel 32. The valve 60 is opened and, as shown in FIG. 6, a bolus 36 of radioactive material advanced into blood vessel 32 by saline solution 76.

Throughout a clinical study of a patient with whom the radioactive bolus injection procedure is used, the lead shield 68 provides effective radiation protection for the entire medical staff during the administration of the radioactive injection. Undesirable radiation exposure as might occur using the described prior art devices and procedure thus advantageously avoided.

In certain cases, the size of the desired bolus of material drawn into retainer 52 may be less than the volume of bolus chamber 54. Care must then be taken to avoid leaving an excessive amount of air in chamber 54. One procedure to avoid such air involves drawing in of a slug of saline solution in front of the bolus 36 to fill in most of the excess volume capacity of the bolus chamber while the first syringe 66 is still attached to end 58.

A preferred technique, however, employs a bolus retainer 52 whose bolus chamber 54 is sized commensurate with the desired amount of bolus material. One can in such case fill the bolus retainer 52 to full capacity, causing only a negligible amount of air from the volume enclosed between end 58 and valve 60. For this reason, a plurality of differently sized bolus retainers 52 are provided and this simplifies the bolus injection procedure.

Figure 7:
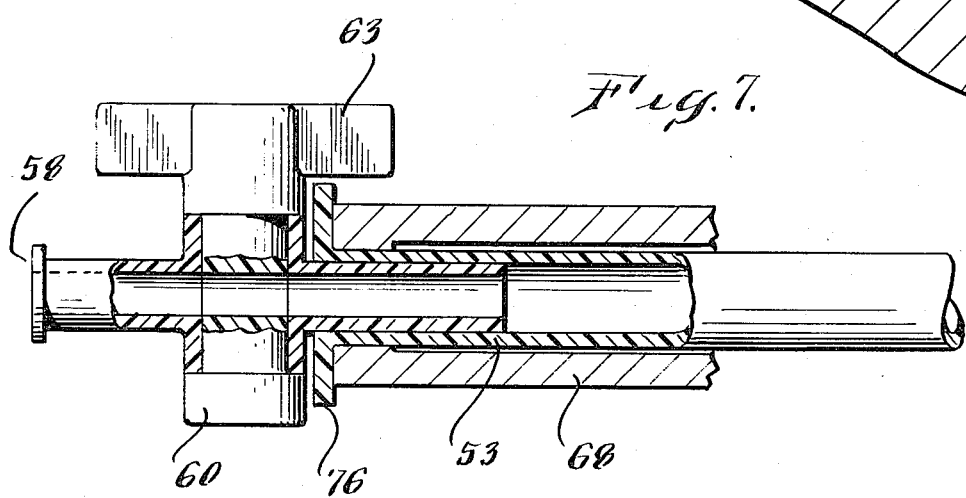
FIG. 7 is an enlarged partial sectional view of a portion of one bolus retainer in accordance with the invention.
Figure 8:
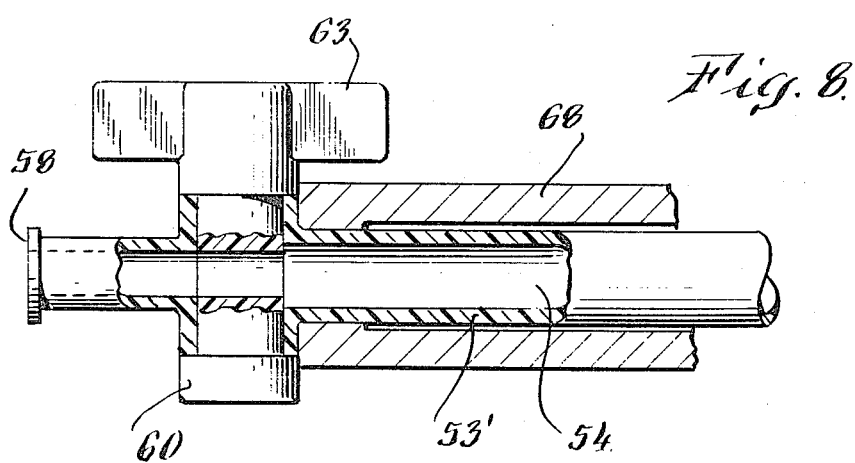
FIG. 8 is an enlarged sectional view of a portion of another bolus retainer in accordance with the invention.

FIGS. 7 and 8 show slightly different versions for a bolus retainer 52. In FIG. 7 a conventional valve 60 is shown frictionally attached to a separate cylindrically shaped body 53 having a flange 76 against which shield 68 is seated. In FIG. 8 the valve 60 is an integrally molded part of cylindrical bolus retaining body 53'.

Having thus explained devices and techniques accordance with the invention, its advantages can be appreciated. Variations may be made by one skilled in the art without departing from the scope of the following claims. For example, the bolus retainer may be used to inject other than radioactive materials.

What is claimed is:

1. A device for use in the injection of a bolus of radioactive material in a blood vessel comprising:
    a longitudinal bolus retainer having a bolus chamber extending between front and rear ends of the bolus retainer, a manually controlled valve located near the rear end of the bolus retainer to open and close said chamber near said rear end, the portion of the bolus chamber between the valve and the front end being capable of retaining a desired volume of said bolus material;
    said bolus retainer being shaped to fit within a radioactive shield for radiation shielding thereby;
    wherein said front end of the bolus retainer has an opening in unrestricted fluid communication with the bolus chamber to receive therein and discharge therefrom a bolus of said radioactive materials, said front end of the bolus retainer further being shaped to receive and retain a hypodermic needle assembly; and
    wherein said rear end of the bolus retainer is shaped to operatively releasably receive a syringe.

2. A method for injecting a bolus of radioactive material into a body comprising the steps of
    mounting a first syringe on a rear end of a longitudinal bolus retainer having a bolus chamber extending between front and rear ends of the bolus retainer and having a manually controlled valve located near said rear end to open or close the bolus chamber near said rear end;
    placing a hypodermic needle at said front end;
    placing a radiation shield over said bolus chamber;
    opening said valve;
    actuating said first syringe to enter through said front end a predetermined quantity of said bolus of radioactive material into the bolus chamber;
    closing said valve;
    replacing said syringe with a flushing syringe containing a flush solution;
    advancing the flush solution from the flushing syringe to inject said bolus while said radiation shield remains in place.

3. The method for injecting a bolus as set forth in claim 3 and further including after said bolus of radioactive material has been entered into said through bore, the step of actuating the first syringe to move said bolus and place in front thereof a predetermined quantity of flushing solution to effectively fill said bolus chamber.

* * * * *